United States Patent
Yano et al.

(10) Patent No.: US 12,390,176 B2
(45) Date of Patent: Aug. 19, 2025

(54) RADIATION DETECTING DEVICE

(71) Applicant: Konica Minolta, Inc., Tokyo (JP)

(72) Inventors: Yuuri Yano, Kokubunji (JP); Hiroshi Utsunomiya, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 58 days.

(21) Appl. No.: 17/847,482

(22) Filed: Jun. 23, 2022

(65) Prior Publication Data

US 2022/0409154 A1 Dec. 29, 2022

(30) Foreign Application Priority Data

Jun. 24, 2021 (JP) ................. 2021-104829

(51) Int. Cl.
*A61B 6/42* (2024.01)
*A61B 6/00* (2024.01)

(52) U.S. Cl.
CPC .......... *A61B 6/4208* (2013.01); *A61B 6/4283* (2013.01); *A61B 6/44* (2013.01)

(58) Field of Classification Search
None
See application file for complete search history.

(56) References Cited

U.S. PATENT DOCUMENTS

| | | | | |
|---|---|---|---|---|
| 6,825,472 B2 * | 11/2004 | Endo | ....... | G01T 1/244 250/336.1 |
| 6,897,449 B1 * | 5/2005 | Hata | ....... | G01T 1/2928 250/370.11 |
| 7,202,481 B2 * | 4/2007 | Spahn | ....... | H04N 23/54 250/580 |
| 7,265,371 B2 * | 9/2007 | Shoji | ....... | B32B 27/08 250/581 |
| 7,514,703 B2 * | 4/2009 | Iwakiri | ....... | G03B 42/02 250/584 |
| 7,569,831 B2 * | 8/2009 | Jadrich | ....... | G03B 42/04 250/370.11 |

(Continued)

FOREIGN PATENT DOCUMENTS

| | | |
|---|---|---|
| CN | 103472479 A | 12/2013 |
| CN | 108966642 A | 12/2018 |

(Continued)

OTHER PUBLICATIONS

JPO Notice of Reasons for Refusal for corresponding JP Application No. 2021-104829; Issued Dec. 24, 2024.

(Continued)

*Primary Examiner* — David P Porta
*Assistant Examiner* — Djura Malevic
(74) *Attorney, Agent, or Firm* — CANTOR COLBURN LLP

(57) ABSTRACT

A radiation detecting device including: a radiation detector that includes a board having a flexibility and a semiconductor element formed on an imaging surface of the board; a supporter that supports the radiation detector; a housing that includes a front part facing the imaging surface and a rear part facing the front part across the radiation detector and that houses the radiation detector; and a cushion that is provided at least one of between the supporter and the radiation detector and between the supporter and the rear part.

15 Claims, 1 Drawing Sheet

(56) References Cited

U.S. PATENT DOCUMENTS

| | | | |
|---|---|---|---|
| 7,582,877 B2* | 9/2009 | Dobrusskin | G03B 42/04 250/370.09 |
| 7,638,773 B2* | 12/2009 | Kuwabara | G03B 42/04 250/370.08 |
| 7,663,114 B2* | 2/2010 | Aoyagi | G01T 1/2928 250/370.09 |
| 7,800,065 B2 | 9/2010 | Konkle | H01L 27/14618 250/336.1 |
| 7,947,960 B2* | 5/2011 | Wu | G03B 42/02 250/370.09 |
| 8,744,044 B2* | 6/2014 | Suwa | A61B 6/00 378/62 |
| 8,823,042 B2* | 9/2014 | Kim | H10K 59/00 438/23 |
| 8,929,510 B2* | 1/2015 | Nishino | A61B 6/4405 378/102 |
| 9,104,097 B2* | 8/2015 | Suwa | A61B 6/4283 |
| 9,168,016 B2* | 10/2015 | Ohta | A61B 6/4405 |
| 9,535,165 B2* | 1/2017 | Takatori | G01T 1/17 |
| 9,702,986 B2* | 7/2017 | Peters | G01T 1/2006 |
| 9,864,078 B2* | 1/2018 | Sumi | G03B 42/04 |
| 9,978,234 B2 | 5/2018 | Kano | G01T 1/244 |
| 10,024,980 B2* | 7/2018 | Suzuki | G01T 1/2006 |
| 10,024,984 B2 | 7/2018 | Ogawa | G01T 1/244 |
| 10,061,042 B2* | 8/2018 | Suzuki | G01T 1/20187 |
| 10,119,859 B2* | 11/2018 | Suzuki | A61B 6/4283 |
| 10,185,039 B2 | 1/2019 | Ergler | G01T 1/243 |
| 10,274,613 B2* | 4/2019 | Suzuki | G01N 23/04 |
| 10,488,532 B2* | 11/2019 | Abenaim | G01T 1/20184 |
| 10,648,854 B2* | 5/2020 | Suzuki | A61B 6/102 |
| 10,722,195 B2* | 7/2020 | Suwa | A61B 6/4283 |
| 10,748,976 B2* | 8/2020 | Nishimura | H01L 23/4985 |
| 10,966,329 B2* | 3/2021 | Park | H10K 59/87 |
| 11,141,120 B2* | 10/2021 | Sakuragi | A61B 6/4208 |
| 11,166,693 B2* | 11/2021 | Saigusa | A61B 6/4208 |
| 11,375,098 B2* | 6/2022 | Saigusa | A61B 6/4233 |
| 11,515,503 B2* | 11/2022 | Shin | H10K 59/87 |
| 11,585,953 B2* | 2/2023 | Ye | G01T 1/2018 |
| 11,740,668 B2* | 8/2023 | Asada | G06F 1/189 361/679.02 |
| 11,774,376 B2* | 10/2023 | Fukushima | G01N 23/04 378/62 |
| 12,105,566 B2* | 10/2024 | Asada | H05K 1/028 |
| 12,161,493 B2* | 12/2024 | Kuriyama | A61B 6/4283 |
| 2002/0014594 A1* | 2/2002 | Endo | G01T 1/244 250/370.09 |
| 2004/0227096 A1* | 11/2004 | Yagi | G01T 1/2928 378/189 |
| 2005/0017188 A1* | 1/2005 | Yagi | G01T 1/244 250/370.09 |
| 2005/0056789 A1* | 3/2005 | Spahn | A61B 6/4233 348/E5.027 |
| 2005/0212935 A1* | 9/2005 | Watanabe | G01T 1/244 348/294 |
| 2007/0138400 A1* | 6/2007 | Ertel | G01T 1/1644 250/370.11 |
| 2007/0272873 A1* | 11/2007 | Jadrich | G01T 1/20 250/370.11 |
| 2008/0078940 A1* | 4/2008 | Castleberry | G01T 1/20189 250/370.09 |
| 2009/0065703 A1* | 3/2009 | Jadrich | G01T 1/2928 250/336.1 |
| 2009/0122959 A1* | 5/2009 | Jadrich | G01T 1/20 378/91 |
| 2009/0202038 A1* | 8/2009 | Wu | A61B 6/4429 378/198 |
| 2009/0202044 A1* | 8/2009 | Wu | A61B 6/4233 378/189 |
| 2010/0001195 A1* | 1/2010 | Konkle | G01T 1/2006 438/64 |
| 2012/0211661 A1* | 8/2012 | Itaya | G01T 1/202 250/367 |
| 2013/0043400 A1* | 2/2013 | Nakatsugawa | A61B 6/4423 250/336.1 |
| 2013/0083900 A1* | 4/2013 | Kobayashi | G01T 1/2019 378/189 |
| 2013/0168564 A1* | 7/2013 | Konkle | A61B 6/102 250/370.08 |
| 2013/0266121 A1* | 10/2013 | Suwa | A61B 6/4283 378/189 |
| 2013/0341597 A1* | 12/2013 | Kim | H05K 1/147 257/40 |
| 2014/0084161 A1* | 3/2014 | Takatori | G03B 42/04 250/336.1 |
| 2014/0124678 A1* | 5/2014 | Yoneyama | A61B 6/4405 250/393 |
| 2015/0083924 A1* | 3/2015 | Okada | H04N 25/766 250/370.08 |
| 2015/0293237 A1* | 10/2015 | Suzuki | G03B 42/04 250/369 |
| 2016/0155526 A1* | 6/2016 | Arimoto | C09K 11/628 250/488.1 |
| 2016/0299241 A1* | 10/2016 | Suzuki | G01T 1/20189 |
| 2017/0038252 A1* | 2/2017 | Suzuki | G01J 1/4228 |
| 2017/0082758 A1* | 3/2017 | Ogawa | G01T 1/2985 |
| 2017/0090044 A1* | 3/2017 | Suzuki | A61B 6/4283 |
| 2017/0309355 A1* | 10/2017 | Lee | G21F 1/085 |
| 2017/0372572 A1* | 12/2017 | Kano | C22C 23/00 |
| 2018/0019035 A1* | 1/2018 | Baturin | G01T 1/2019 |
| 2018/0321392 A1* | 11/2018 | Suzuki | G01T 1/2006 |
| 2019/0011574 A1* | 1/2019 | Suwa | A61B 6/4405 |
| 2019/0018151 A1* | 1/2019 | Kawaguchi | G01T 1/244 |
| 2019/0025116 A1* | 1/2019 | Suzuki | G03B 42/04 |
| 2019/0110376 A1* | 4/2019 | Tagawa | H05K 7/20436 |
| 2019/0146105 A1* | 5/2019 | Clark | G01T 7/00 250/362 |
| 2019/0353805 A1* | 11/2019 | Konkle | G01T 1/247 |
| 2020/0100739 A1* | 4/2020 | Horiuchi | A61B 6/4283 |
| 2020/0187884 A1* | 6/2020 | Sakuragi | A61B 6/4405 |
| 2021/0003722 A1* | 1/2021 | Kato | A61B 6/4208 |
| 2021/0175462 A1* | 6/2021 | Shin | G06F 1/1601 |
| 2021/0199602 A1* | 7/2021 | Fukushima | G01T 1/20 |
| 2022/0249041 A1* | 8/2022 | Suzuki | G01T 1/20 |
| 2022/0409154 A1* | 12/2022 | Yano | A61B 6/4208 |
| 2023/0047362 A1* | 2/2023 | Shin | H10K 77/111 |
| 2023/0273329 A1* | 8/2023 | Otaki | G01T 1/244 250/370.08 |

FOREIGN PATENT DOCUMENTS

| | | |
|---|---|---|
| JP | 2009020099 A | 1/2009 |
| JP | 2011069992 A | 4/2011 |
| JP | 2012048169 A | 3/2012 |
| JP | 2013072646 A | 4/2013 |
| JP | 2020127620 A | 8/2020 |

OTHER PUBLICATIONS

SIPO 1st Office Action for corresponding CN Application No. 202210696404.3; Issued Sep. 4, 2024.

* cited by examiner

RADIATION DETECTING DEVICE

CROSS-REFERENCE TO RELATED APPLICATIONS

The present invention claims priority under 35 U.S.C. § 119 to Japanese Application, 2021-104829, filed on Jun. 24, 2021, the entire contents of which being incorporated herein by reference.

BACKGROUND

Technological Field

The present invention relates to a radiation detecting device.

Description of the Related Art

Conventionally, lightweight, and thin radiation detecting devices called flat panel detectors (FPDs) have been used for radiation (hereinafter, referred to as X-ray) imaging.

The market is still demanding further weight reduction of FPDs. Components that account for a high percentage of the weight of FPD components include glass boards and resin bases. Reducing the weight of these components will lead to lighter FPDs. To reduce weight, thin film transistors (TFTs) are formed on thin film flexible boards from glass boards to reduce the weight of the glass portion. Technology has been established to form the base with foaming agent, which is a lighter material than bases made from resin molding, and further weight reduction can be achieved compared to conventional FPDs.

In JP 2012-048169 A, there is described a technique of attaching, on the opposite side of the surface of the surface attached to the top plate of the radiation detecting device attached to the top plate in an electronic cassette housing, a conductive rubber supported on the opposite side of the top plate of the housing, for the purpose of preventing electrification caused by vibration when the radiation detecting device is carried around.

SUMMARY

Configurations employing TFTs on flexible boards are lighter but less rigid than those employing TFTs on conventional glass boards, making them vulnerable to vibration. Therefore, when the distance between the TFT signal line and the base fluctuates due to vibration, the parasitic capacitance formed in that space fluctuates, noise is superimposed on the X-ray detection unit that detects X-ray exposure and image, resulting in deterioration of image quality and false detection of X-ray exposure.

An object of the present invention is to effectively suppress vibration while maintaining the light weight of the radiation detecting device, and thereby prevent degradation of image quality and improve the detection accuracy of X-ray exposure.

To achieve at least one of the abovementioned objects, according to an aspect of the present invention, a radiation detecting device reflecting one aspect of the present invention is a radiation detecting device including: a radiation detector that includes a board having a flexibility and a semiconductor element formed on an imaging surface of the board; a supporter that supports the radiation detector; a housing that includes a front part facing the imaging surface and a rear part facing the front part across the radiation detector and that houses the radiation detector; and a cushion that is provided at least one of between the supporter and the radiation detector and between the supporter and the rear part.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION OF EMBODIMENTS

Hereinafter, embodiments according to the present invention will be described with reference to the drawings. However, the scope of the invention is not limited to the disclosed embodiments or illustrated examples.

Figure 1:
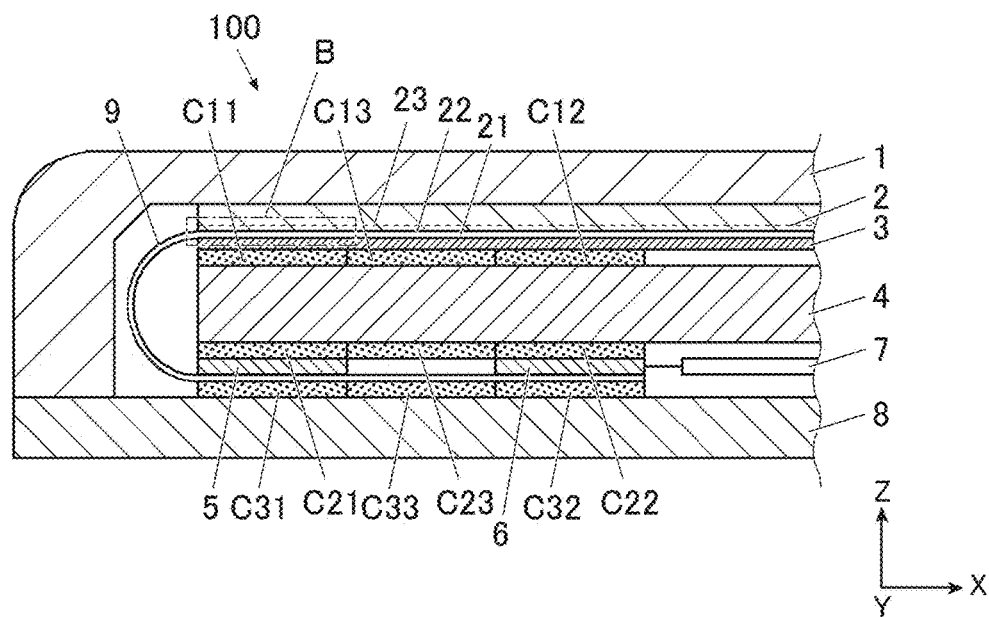
FIG. 1 is a cross-sectional schematic diagram of a radiation detecting device in an embodiment of the present invention.

As shown in FIG. 1, the radiation detecting device 100 of an embodiment of the preset invention has a front part 1 of the housing, a radiation detector (TFT of a flexible board) 2, the radiation shield 3, a supporter (base) 4, a circuit board 5, an interface board 6, a control board 7, a rear part 8 of the housing, and a flexible printed board 9. There is a cushion material between the front part 1 and the radiation detector 2.

The horizontal direction of the radiation detecting device 100 is illustrated as X, the vertical direction as Y, and the front-rear direction as Z.

As shown in FIG. 1, the front part 1, the radiation detector 2, the radiation shield 3, the supporter 4, the circuit board 5 (interface board 6, control board 7), and the rear part 8 are layered in the Z direction.

The circuit board 5 has a readout circuit that reads the signals from the radiation detector. The radiation detector 2 and the circuit board 5 are connected by a flexible printed board 9. The flexible printed board 9 has a printed conduction pattern connecting the radiation detector 2 to the circuit board 5 and is bent and pulled around the Y-axis from the radiation detector 2 to the circuit board 5.

The radiation detector 2 has a flexible board 21 and a semiconductor element 23 formed on an imaging surface 22 of the board 21. The radiation detector 2 includes a plurality of radiation detecting elements arranged in a two-dimensional array on the XY plane to detect radiation. The radiation detecting elements are semiconductor devices such as photodiodes and phototransistors. The radiation detecting elements generate an electrical charge corresponding to the amount of radiation exposure. Switch elements composed of thin film transistors (TFT) are connected one-to-one to the radiation detecting elements, which are also arranged two-dimensionally on the XY plane. By controlling the on/off timing of such switch elements, the detected analog signals of the radiation detecting elements in each row in the Y direction are sent to each readout circuit on the circuit board 5 through signal lines extending in the Y direction.

Each readout circuit generates an analog signal value based on the amount of charge input from the corresponding signal line.

Analog signal values output from each readout circuit are sequentially sent to the interface board 6. The interface board 6 processes the signals from the circuit board 5. The interface board 6 converts analog signal values from the circuit board 5 to predetermined digital signal values and sends them to the control board 7.

The control circuit mounted on the control board 7 controls radiation imaging, and the readout circuit on the circuit board 5 reads out and the interface board 6 generates image data of radiation image based on the A/D-converted signal values. In other words, the control circuit has the function of generating image data based on the signal from the radiation detector 2.

The control circuit has the function of detecting the radiation exposure based on the signal from the radiation detector 2 in order to control the radiation imaging. The control circuit has a function to detect radiation exposure based on the signal from the radiation detector 2 in synchronization with the timing that radiation is emitted toward the radiation detector 2 from the radiation generator placed opposite to the radiation detector 2 across the subject. The elements that detect radiation exposure may be installed separately from the radiation detecting elements that generate image data.

The flexible board of the radiation detector 2 is composed of a resin film. The radiation detector 2 may include a scintillator on a layer of semiconductor element 23 that includes the radiation detecting elements and TFTs described above.

The supporter 4 is a foam body in the shape of a plate and supports the radiation detector 2 in a flat standard form.

The housing has the front part 1 facing the imaging surface 22 and the rear part 8 facing the front part 1 across the radiation detector 2 and houses the radiation detector 2.

The radiation shield 3 is composed of a sheet of lead, molybdenum, or tungsten, for example.

The configuration that employs the flexible board TFT and foam base as in the present embodiment is lighter in weight than the conventional configuration that employs the glass board TFT and resin base, but it is less rigid and vulnerable to vibration. Therefore, if the distance between the TFT signal line and the base varies due to vibration, the parasitic capacitance formed in that space fluctuates, causing noise to be superimposed on the image and the X-ray detector, resulting in degradation of image quality and false detection of X-ray exposure as described above.

The inventors' research has shown that it is effective to suppress vibration at the connection site B between the radiation detector 2 and the flexible printed board 9, which is extended from the radiation detector 2 to the circuit board 5 with the readout circuit, in order to reduce the influence of noise on the detection signal for detecting X-ray exposure and to improve detection accuracy in a configuration that employs the flexible board TFT and foam base.

For example, if a large shock is applied from the front part 1, this connection site B will vibrate and generate noise.

In addition, vibrations are transmitted through the supporter 4 to the circuit board 5, interface board 6, and flexible printed board 9 on the rear part 8 side, which goes around to vibrate the connection site B, resulting in noise generation.

In order to suppress vibration, the radiation detecting device 100 in this embodiment includes cushions C11, C12, C21, C22, C31, C32 in whole or in part selectively. The cushion C11 and the cushion C12 are in the same layer, and when both are installed, they may be used as one continuous piece of the cushion, including the cushion C13 between them. The cushion C21 and the cushion C22 are in the same layer, and when both are installed, they may be used as one continuous piece of the cushion, including the cushion C23 between them. The cushion C31 and the cushion C32 are in the same layer, and when both are installed, they may be used as one continuous piece of the cushion, including the cushion C33 between them. The cushion may be further provided or extended to other ranges.

The cushions C11 to C13 are provided between the supporter 4 and the radiation detector 2.

The cushions C21 to C23 and C31 to C33 are provided between the supporter 4 and the rear part 8. Among them, the cushions C21 to C23 is provided between the supporter 4 and the portion including the circuit board 5 and interface board 6. The cushions C31 to C33 are provided between the rear part 8 and the portion including the circuit board 5 and interface board 6.

The cushion is provided at least one of between the supporter 4 and the radiation detector 2, and between the supporter 4 and the rear part 8.

The cushion may be provided between the supporter 4 and the radiation detector 2 and between the supporter 4 and the rear part 8. Vibrations can be better suppressed.

The radiation shield 3 is provided between the radiation detector 2 and the supporter 4.

The cushions C11 to C13 are provided between the radiation shield 3 and the supporter 4.

When limiting, to the cushions C11 to C13, the cushion placed in this layer for reducing weight, the cushion is limited to either or both the cushion C11 and the cushion C12 in some cases. Even in these cases, the locally placed cushion does not directly contact the radiation detector 2 due to the intervention of the radiation shield 3. This suppresses local deformation of the radiation detector 2 and reduces the occurrence of image irregularities caused by this deformation.

Figure 2:
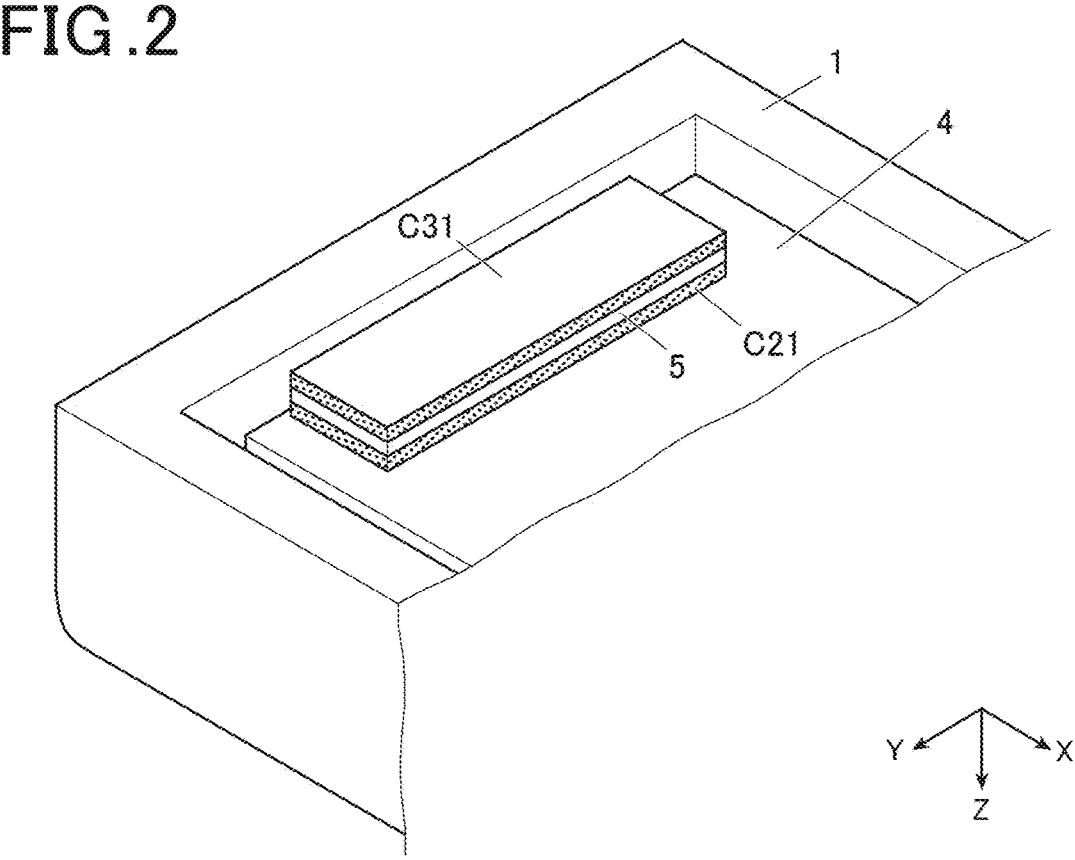
FIG. 2 is a diagram viewed from the rear side to show the layered structure of the circuit board, its upper and lower cushions, and supporter.

FIG. 2 shows a perspective diagram viewed from the rear side to show the layered structure of the circuit board 5 and its upper and lower cushions, as well as the supporter 4.

To effectively suppress vibration, the cushion may be provided between the supporter 4 and the circuit board 5, at least in a position overlapping the circuit board 5 in the Z-direction, as in the cushion C21.

Furthermore, the cushion may be provided between the supporter 4 and the interface board 6, as in the cushion C22.

Also, as in the cushion C31, the cushion may be provided between the circuit board 5 and the rear part 8, at least in the position overlapping the circuit board 5 in the Z-direction.

Furthermore, the cushion may be provided between the interface board 6 and the rear part 8, as in the cushion C32.

To improve detection accuracy by effectively suppressing vibration while noticeably maintaining the light weight, only the cushion C11 or the cushion C21 may be provided. By effectively suppressing vibration at the connection site B, noise effects on the detection signal can be reduced and detection accuracy can be improved.

The cushions C11 to C13, C21 to C23, and C31 to C33 can be rigid bodies such as plates molded from polycarbonate, ABS resin, carbon fiber reinforced resin, and metal foam.

The cushions C11 to C13, C21 to C23, and C31 to C33 can be elastic bodies such as ethylene-propylene, chloroprene, styrene, ophylene, and polyurethane elastomers.

The cushions C11 to C13, C21 to C23, and C31 to C33 can be foam bodies made of polyethylene, polypropylene, polystyrene, etc.

In particular, the cushions C11 to C13 are made rigid to function as a spacer to maintain the distance between the radiation shield 3 and the supporter 4, thereby suppressing parasitic capacitance changes.

As described above, according to the radiation detecting device 100 in this embodiment, while employing the light-weight flexible board TFT (2) and the foam base (4), vibration that affects detection accuracy can be effectively suppressed by limiting the placement of the cushion in appropriate locations. Thus, it is possible to prevent deterioration of image quality and improve the detection accuracy of X-ray exposure by effectively suppress the vibration while maintaining the light weight of the radiation detecting device 100.

Although embodiments of the present invention have been described and illustrated in detail, the disclosed embodiments are made for purposes of illustration and example only and not limitation. The scope of the present invention should be interpreted by terms of the appended claims.

What is claimed is:

1. A radiation detecting device comprising:
   a radiation detector that includes a board having a flexibility and a semiconductor element formed on an imaging surface of the board;
   a supporter that supports the radiation detector;
   a housing that includes a front part facing the imaging surface and a rear part facing the front part across the radiation detector and that houses the radiation detector;
   a circuit board operably connected the radiation detector;
   a flexible printed board that connects the radiation detector and the circuit board at a connection site; and
   at least one cushion provided between the supporter and the circuit board,
   wherein the connection site, the at least one cushion, and the circuit board are provided in a position overlapping each other with respect to the direction of radiation.

2. The radiation detecting device according to claim 1, wherein the supporter is formed of a foam body.

3. The radiation detecting device according to claim 1, wherein the at least one cushion is provided between the supporter and the radiation detector and between the supporter and the rear part.

4. The radiation detecting device according to claim 1, further comprising a radiation shield that is provided between the radiation detector and the supporter, wherein the at least one cushion is provided between the radiation shield and the supporter.

5. The radiation detecting device according to claim 1, wherein the circuit board is provided with a readout circuit that reads out a signal from the radiation detector, and wherein the cushion is provided at least in a position overlapping the circuit board between the supporter and the circuit board.

6. The radiation detecting device according to claim 5, further comprising an interface board that processes a signal from the circuit board, wherein the cushion is provided between the supporter and the interface board.

7. The radiation detecting device according to claim 1, wherein the circuit board is provided with a readout circuit that reads out a signal from the radiation detector, wherein the cushion is provided at least in a position overlapping the circuit board between the circuit board and the rear part.

8. The radiation detecting device according to claim 7, further comprising an interface board that processes a signal from the circuit board, wherein the cushion is provided between the interface board and the rear part.

9. The radiation detecting device according to claim 1, wherein
   the radiation detecting device generates image data based on a signal from the radiation detector, and
   the radiation detecting device detects radiation exposure.

10. The radiation detecting device according to claim 1, wherein the at least one cushion includes a rigid body.

11. The radiation detecting device according to claim 1, wherein the at least one cushion includes is an elastic body.

12. The radiation detecting device according to claim 1, wherein the at least one cushion includes is a foam body.

13. The radiation detecting device according to claim 9claim 1, wherein the flexible printed board includes a front portion, a middle portion and a rear portion, wherein the middle portion is bent, the front portion extends between the supporter and the front part of the housing, and the rear portion extends between the supporter and the rear part of the housing.

14. The radiation detecting device according to claim 1, wherein portions of an inner surface of the front part of the housing are free from contact with any cushion.

15. The radiation detecting device according to claim 1, wherein the at least one cushion is provided between the circuit board and the rear part, and is provided in a position overlapping the connection site.

* * * * *